United States Patent [19]

Stockdale et al.

[11] 4,283,141

[45] Aug. 11, 1981

[54] SAMPLE CELL AND STIRRER FOR SPECTROPHOTOMETRY

[75] Inventors: Trevor J. Stockdale; Anthony R. L. Moss, both of Cambridge, England

[73] Assignee: Pye (Electronic Products) Limited, Cambridge, England

[21] Appl. No.: 9,211

[22] Filed: Feb. 5, 1979

[30] Foreign Application Priority Data

Feb. 13, 1978 [GB] United Kingdom ............... 05620/78

[51] Int. Cl.³ .............................................. G01N 1/00
[52] U.S. Cl. .................................... 356/246; 356/427
[58] Field of Search ................. 356/246, 427, 337–339

[56] References Cited

U.S. PATENT DOCUMENTS

| 3,966,333 | 6/1976 | Marcus | 356/246 |
| 4,125,327 | 11/1978 | Margolis | 356/427 |

Primary Examiner—John K. Corbin
Assistant Examiner—Bruce Y. Arnold
Attorney, Agent, or Firm—Thomas A. Briody; Robert T. Mayer; Paul R. Miller

[57] ABSTRACT

A displaceable combination of a sample solution cell and a one-piece plastic stirrer is provided for spectrophotometry. The cell has an opening at one end through which the stirrer is inserted and arranged for reciprocation in the cell by engagement of a portion outside the cell. The stirrer is also arranged to sit in the cell during passage of radiation therethrough upon spectrophotographic measurement of the sample.

17 Claims, 4 Drawing Figures

U.S. Patent   Aug. 11, 1981   4,283,141
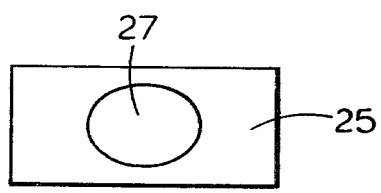
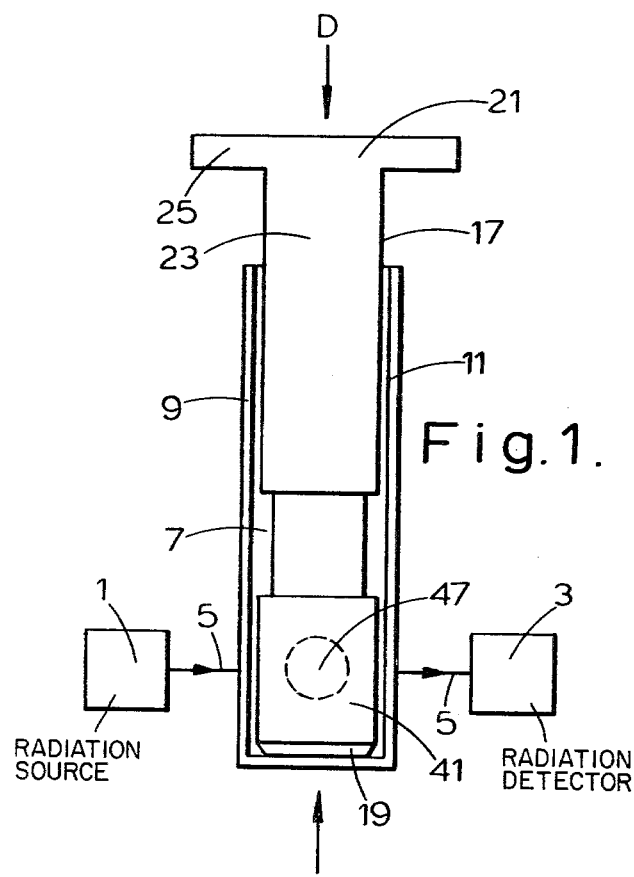
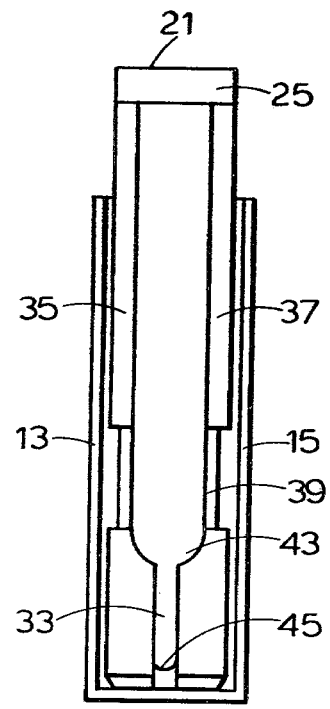
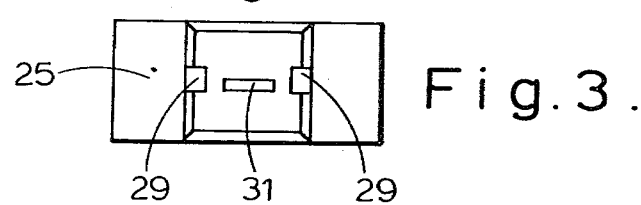

SAMPLE CELL AND STIRRER FOR SPECTROPHOTOMETRY

The present invention relates to a sample cell for use in spectrophotometric instruments and a stirrer for stirring solutions within the cell.

In spectrophotometric analysis a beam of light is most often passed through a transparent sample cell containing a solution of the sample under analysis and the degree of optical change in the beam passing through the sample cell is measured.

Some sample solutions need stirring prior to measurement to ensure homogeniety and, in some analyses, to mix a reagent with the sample solution prior to measurement.

In the case of one type of known sample cell, stirring has been effected by means of an individual rotatable bar magnet within the sample cell arranged to rotate under the control of an external magnetic field. In the case of other known cells not containing stirrer elements, stirring has been effected by means of an external retractable stirrer inserted into a series of sample cells in succession.

Often in spectrophotometric analysis a large number of samples, requiring a correspondingly large number of sample cells, are examined automatically or semi-automatically. With sample cells containing rotatable magnets, cost prevents the magnets being treated as disposable items and cross-contamination upon reuse of the sample cells can occur. Where a retractable stirrer is used sample cells can be disposed of after use, but cross-contamination and atmospheric contamination can take place as a result of using a common stirrer for each cell. When medical samples are analysed, the re-use of either sample cells or stirrers may be an unacceptable health hazard for laboratory staff.

An additional drawback to using cells containing a rotatable magnet is the interference which can be caused to the detector and to electronic circuitry of the spectrophotometer by the external magnetic field which drives the rotatable magnet.

An object of the present invention is to provide a sample cell and stirrer combination which will overcome the foregoing shortcomings of prior art sample cells and stirrers.

According to one aspect of the invention there is provided a combination of a sample cell and stirrer arranged to be positioned in a radiation path of a spectrophotometric instrument and to permit the passage of radiation therethrough, wherein the sample cell has an opening through which the stirrer is inserted, wherein the stirrer is a one-piece plastic moulding arranged to sit in the sample cell during the spectrophotometric measurement, wherein a portion of the stirrer is arranged for reciprocation within the cell in a direction perpendicular to the plane of the opening to stir sample solution within the cell prior to such measurement, and wherein a portion of the stirrer is arranged for engagement outside the cell by separate reciprocating means. The cell may have a rectangular cross-section with the stirrer of generally rectangular configuration perpendicular to the direction of reciprocation, and the stirrer preferably comprises a pair of opposed parallel limbs joined at or adjacent both the inner and outer ends thereof, the stirrer being positioned in the cell to permit radiation to pass between the limbs during the measurement.

To enable the combination to be employed in, for example, fluorescence spectroscopy one of the limbs of the stirrer may include an aperture to permit the passage of radiation scattered normal to the incident radiation entering the cell.

The limbs of the stirrer may be shaped to minimise migration of sample solution from the examination zone of the sample cell by capillary action between the limbs and adjacent faces of the sample cell; and the region of the limbs of the stirrer lying in the examination zone of the sample cell may be shaped to minimise the volume of sample solution required for spectrophotometric analysis. In addition the limbs of the stirrer may be shaped adjacent the examination zone to enable the ready draining back of displaced sample solution into the examination zone preferably by providing smooth transition from a region of lesser to a region of greater cross-sectional area of the stirrer.

The inner end of the stirrer preferably includes an aperture to enable sample solution to be readily displaced from below the stirrer into the space between the limbs upon reciprocation and the outer end preferably includes an aperture through which sample solution may be introduced into the sample cell enabling the sample cell and stirrer combination to be filled and/or emptied with the stirrer in position in the cell. The outer end of the stirrer is also preferably shaped to permit ready engagement by reciprocating means.

According to another aspect of the invention a stirrer of the aforementioned type is defined.

A sample cell and stirrer combination in accordance with the invention will now be described with reference to the accompanying drawings of which:

FIG. 1 is a diagrammatic representation of a spectrophotometer including an elevation view of a sample cell and stirrer combination according to the present invention;

FIG. 2 is a view of the sample cell and stirrer combination of FIG. 1 along path 5 of FIG. 1 in the direction indicated by the arrow;

FIG. 3 is a plan view of the stirrer of FIG. 1 looking in the direction C;

FIG. 4 is a plan view of the stirrer of FIG. 1 looking in the direction D.

There are various types of spectrophotometric instruments operating upon the same general principle, that is a sample solution is put into a sample cell disposed in the path of a beam of light or other radiation. The optical change produced in the radiation beam by the sample solution is then measured. The principal requirement for such measurements is that the sample cell is filled with sufficient sample solution to ensure that a beam of radiation of known cross-sectional area traverses the sample solution for a predetermined distance. It is preferred for the sample cell to have optically flat parallel planar faces through which the radiation beam is to pass which has led to the general use of sample cells of square or rectangular cross-section.

The spectrophotometric system shown diagrammatically in FIG. 1 is representative of most forms of spectrophotometric instrument and comprises a radiation source 1 and a radiation detector 3. Conventional optical elements (not shown) are provided so that radiation from source 1 follows a predetermined path 5 through the instrument to detector 3. Radiation source 1 and radiation detector 3 are normally provided with associated electronic and electrical circuitry not here shown or described as for the purposes of the present invention such circuitry may be completely conventional.

Suitably interposed between radiation source 1 and radiation detector 3 is a sample cell 7 of square cross-section having parallel planar walls 9 and 11 of radiation permeable material through which radiation in path 5 passes in traversing the cell. Cell 7 may be a conventional sample cell having one open end and in accordance with normal practice walls 13 and 15 may be obscured.

A stirrer according to the present invention, generally indicated at 17, is a one piece plastic moulding which sits within the sample cell 7, and when in this position the inner end 19 of the stirrer 17 contacts the closed end of the cell 7 and the outer end 21 and a portion 23 of the body of stirrer 17 protrudes from the open end of sample cell 7. The end 21 of the stirrer 17 is provided with a flange 25 and is apertured at 27. The end 19 is chamfered and provided with lateral slots 29 and an aperture 31, all of which communicate with the sample examination region 33 traversed by the radiation beam 5 when the sample cell 7 is positioned within a spectrophotometric instrument.

The body 23 of the stirrer 17 consists of two identical opposed limbs 35 and 37 both reduced in cross-sectional area in a region 39 and increased in cross-sectional area in a region 41 in the manner shown in FIGS. 1 and 2 of the drawing. The limbs 35 and 37 are also both radiussed at 43 as is the floor 45 of the examination zone 33 enclosed between the limbs.

In operation sample solution and any reagents are introduced into the sample cell 7 through the aperture 27 in the outer end 21 of stirrer 17 i.e. the sample cell can be inserted into or brought to the filling and measuring position of the spectrophotometer with the stirrer already inserted in it, a feature of considerable advantage when the combination is employed with automatic or semi-automatic instruments.

Prior to spectrophotometric measurement the contents of the cell 7 are stirred by reciprocating the stirrer 17 within the cell in a direction perpendicular to the plane of the opening, either manually or automatically, by suitable separate reciprocating means engaging flange 25. Both the cell 7 and its individual stirrer 17 may be discarded after the measurement. Further advantages of the above-described cell and stirrer are described below.

Effective stirring and measurement of solutions injected into the sample cell 7 is enhanced by means of the cell and stirrer combination described above. For example, reciprocation of stirrer 17 causes sample solution to be almost completely displaced from the floor of the sample cell, ensuring displacement of any suspended solids which might tend to settle out of the solution to be examined. The vortices produced by rapid movement of the sample solution through slots 29 and aperture 31 considerably assist the effectiveness of the stirring. It has been found that the configuration of the stirrer 17 enables even turbid solution to be effectively mixed, with as few as four or five reciprocal movements, to give a homogeneous sample solution for measurement.

The configuration of the stirrer 17 also enables extremely small sample solution volumes to be accommodated and measured within standard spectrophotometric sample cells. By providing a considerable bulk of material in limbs 35 and 37 in the region 41 of stirrer 17, small sample quantities injected into the sample cell fill the examination zone 33 through which radiation beam 5 of the spectrophotometer passes. In many analyses particularly of biological or body fluids the amount of solution available for measurement may be extremely small. Using a stirrer having the configuration of the stirrer 17 as herein described in a 10 mm×10 mm×45 mm sample cell sample volumes as small as 0.5 milliliters have been effectively examined using the whole beam area of the spectrophotometer. An additional advantage of using extremely small sample volumes is the reduced amount of reagents required for analyses, such reagents often being extremely costly.

The reduced cross-sectional area of the limbs of the stirrer 17 in the region 39 minimises capillary action between the limbs 35 and 37 and the sample cell walls which could cause migration of the sample solution away from the examination zone 33 after the sample has been stirred. The region 43 is radiussed as illustrated to ensure rapid draining back of displaced sample solution into examination zone 33 after stirring. The floor 45 of examination zone 33 is radiussed to prevent the retention of air bubbles which could cause measurement anomalies.

The stirrer 17 is conveniently moulded of high impact polystyrene Type 5MA with a matt black surface finish to minimise spurious reflections within the sample cell.

Although the invention has been described with specific reference to absorption or transmission spectrophotometry it will be apparent to those skilled in the art that sample cell and stirrer combinations and stirrers therefor in accordance with the invention may be used in other spectrophotmetric techniques. For example, in fluorescence spectrophotometry, by providing an aperture such as is shown in dotted outline at 47 in FIG. 1 on the limb 37 of stirrer 17, fluorescent radiation is emitted by a sample solution, in response to incident radiation from source 1, emerges from such aperture normal to the incident beam.

Although the invention has been described with specific reference to sample cells of square cross-section it will be understood that sample cells of rectangular or other cross-section may equally well be employed.

We claim:

1. A cell arrangement for spectrometric instruments comprising a sample cell positioned in a radiation path for permitting passage of radiation; a one-piece plastic stirrer positioned in a radiation transmissive region of said sample cell, said stirrer comprising: a body portion having opposed limbs extending exterior to said sample cell, said body portion including a flange at its outer end having an aperture therein to provide a path for fluid to communicate freely with the interior of said sample cell; said flange designed to permit reciprocating said stirrer in said sample cell in a direction perpendicular to the direction of the radiation path; said opposed limbs including, within the interior of said sample cell, an intermediate region of reduced cross-sectional dimensions, and an inner-end-region of substantially increased cross-sectional dimensions; said inner-end-regions of said opposed limbs being spaced apart to permit radiation to pass therethrough and including a chamfered end-portion for contacting closed end of said sample cell.

2. A cell arrangement according to claim 1, wherein the inner surfaces of said stirrer inner-end region are shaped to form a small examination zone.

3. A cell arrangement according to claim 2, wherein said small examination zone enables accommodation of extremely small amounts of sample solution.

4. A cell arrangement according to claim 1, wherein said intermediate regions of said opposed limbs of said stirrer minimize capillary movement of said sample solution away from an examination zone.

5. A cell arrangement according to claim 1, wherein said stirrer includes internal zones between said opposed limbs which are shaped to permit rapid draining back of said sample solution to an examination zone after stirring.

6. A cell arrangement according to claim 1, wherein a small examination zone is formed between internal portions of said opposed limbs of said stirrer, said examination zone having a curved floor to minimize the formation of air bubbles in said sample solution.

7. A cell arrangement according to claim 1, wherein at least one of said opposed limbs has an aperture permitting passage of radiation scattered in a direction normal to the incident radiation entering said sample cell during measurement.

8. A cell arrangement according to claim 1, wherein said opposed limb, inner-end region includes an aperture for enabling displacement of said sample solution from below said stirrer to an internal space between said opposed limbs during reciprocation of said stirrer.

9. A cell arrangement according to claim 1, wherein said sample cell has a rectangular cross-section, and said stirrer has a rectangular configuration perpendicular to directions of reciprocation.

10. A cell arrangement according to claim 1, wherein said opposed limbs of said stirrer have a smooth transition of inner surfaces between said respective intermediate and inner-end regions.

11. A stirrer for use in conjunction with a sample cell of a spectrophotometer comprising: a body portion having opposed limbs, said limbs including an intermediate region of reduced cross-sectional dimensions; and an inner-end region of substantially increased cross-sectional dimensions; said opposed limbs being spaced apart from each other and having a chamfered end.

12. A stirrer according to claim 11, wherein said inner surfaces of said opposed limbs are shaped to form a small examination zone.

13. A stirrer according to claim 12, wherein said small examination zone has a curved floor.

14. A stirrer according to claim 12, wherein said pair of opposed limbs provide a smooth transition of inner surfaces.

15. A stirrer according to claim 11, wherein at least one of said opposed limbs has a radiation transmissive aperture in the direction facing the other limb.

16. A stirrer according to claim 11, wherein said inner-end region includes a radiation transmissive aperture.

17. A stirrer according to claim 11, wherein said pair of opposed limbs form a generally rectangular configuration perpendicular to a longitudinal direction.

* * * * *